US012557798B2

(12) United States Patent
Unger et al.

(10) Patent No.: US 12,557,798 B2
(45) Date of Patent: Feb. 24, 2026

(54) FLY CAGE MODULE WITH CONVEYOR BELT

(71) Applicant: Livin Farms AgriFood GmbH, Vienna (AT)

(72) Inventors: Katharina Unger, Vienna (AT); Jürgen Wixler, Dissen am Teutoburger Wald (DE)

(73) Assignee: Livin Farms AgriFood GmbH, Vienna (AT)

( * ) Notice: Subject to any disclaimer, the term of this patent is extended or adjusted under 35 U.S.C. 154(b) by 0 days.

(21) Appl. No.: 18/883,217

(22) Filed: Sep. 12, 2024

(65) Prior Publication Data

US 2025/0081949 A1     Mar. 13, 2025

(30) Foreign Application Priority Data

Sep. 13, 2023   (EP) ..................................... 23197147

(51) Int. Cl.
    *A01K 67/30*         (2025.01)
(52) U.S. Cl.
    CPC ........ *A01K 67/30* (2025.01); *A01K 2227/706* (2013.01)
(58) Field of Classification Search
    CPC ........................... A01K 67/30; A01K 2227/706
    See application file for complete search history.

(56) References Cited

U.S. PATENT DOCUMENTS

| | | | | |
|---|---|---|---|---|
| 10,188,084 B2 * | 1/2019 | Leo | ......................... | A01K 67/30 |
| 2018/0035624 A1 * | 2/2018 | Itoh | ......................... | A01G 7/045 |
| 2018/0092339 A1 * | 4/2018 | Massaro | ................ | A01K 67/30 |
| 2019/0191678 A1 | 6/2019 | Alrayya | | |
| 2019/0387704 A1 * | 12/2019 | Hall | ....................... | A01K 67/30 |

(Continued)

FOREIGN PATENT DOCUMENTS

| | | |
|---|---|---|
| CN | 105340843 | 2/2016 |
| CN | 112335611 | 2/2021 |

(Continued)

OTHER PUBLICATIONS

Europe Search Report/Office Action (EP SR/OA) conducted in counterpart Europe Appln. No. 23197147.4 (Mar. 12, 2024).

*Primary Examiner* — Monica L Perry
*Assistant Examiner* — Aaron M Rodziwicz
(74) *Attorney, Agent, or Firm* — GREENBLUM & BERNSTEIN, P.L.C.

(57) ABSTRACT

An apparatus, arrangement and method for producing insect eggs. The apparatus includes a container to accommodate insects in a container interior and prevent the insects from escaping; at least one egg-laying apparatus is arranged in the container and is configured to accommodate insect eggs laid in the container by the insects in the container; and at least one attractant arranged in an area of the at least one egg-laying apparatus that emits stimulants to lure the insects to the at least one egg-laying apparatus to lay the insect eggs. The at least one egg-laying apparatus is at least partially removable from the container, the at least one attractant is spatially separated from the at least one egg-laying apparatus and is separated from the container interior, and wherein the stimulants emitted by the attractant pass through the at least one egg-laying apparatus into the container interior.

20 Claims, 2 Drawing Sheets

(56)  References Cited

U.S. PATENT DOCUMENTS

| | | | |
|---|---|---|---|
| 2022/0304289 A1 | 9/2022 | Jansen et al. | |
| 2022/0408705 A1 | 12/2022 | Roche-Bruyn et al. | |
| 2023/0095722 A1* | 3/2023 | Kawai | A01K 67/30 |
| | | | 119/6.5 |
| 2024/0000053 A1* | 1/2024 | Murata | A01K 67/30 |
| 2024/0032517 A1* | 2/2024 | De Gelder | A01K 67/364 |
| 2024/0049692 A1* | 2/2024 | Atayde | C10B 1/10 |
| 2024/0074417 A1* | 3/2024 | Miura | A01K 67/68 |
| 2025/0010898 A1* | 1/2025 | Peterson | B62B 3/02 |

FOREIGN PATENT DOCUMENTS

| | | |
|---|---|---|
| FR | 3 066 360 | 11/2018 |
| FR | 3 081 677 | 12/2019 |
| WO | 2021/130517 | 7/2021 |
| WO | 2022/081014 | 4/2022 |
| WO | 2023/089142 | 5/2023 |

* cited by examiner

FLY CAGE MODULE WITH CONVEYOR BELT

CROSS-REFERENCE TO RELATED APPLICATION

This application claims priority under 35 U.S.C. § 119(a) to Europe application Ser. No. 23/197,147.4 filed Sep. 13, 2023, the disclosure of which is expressly incorporated by reference herein in its entirety.

BACKGROUND

1. Field of the Invention

Embodiments relate to an apparatus for producing insect eggs, in which a container designed to accommodate insects, in particular adult insects, is provided in an interior of the container and prevents the accommodated insects from escaping from the container. At least one egg-laying apparatus is provided in the container that is designed to accommodate insect eggs that are laid in the container by the insects when the container is used and the at least one egg-laying apparatus is at least partially removable from the container. Embodiments also relate to an arrangement and a method for producing insect eggs.

2. Discussion of Background Information

An insect's life cycle includes several growth stages (e.g. egg, larva, pupa and adult insect), with the duration of these growth stages and the growth stages varying depending on the species of insect. The term "insect" includes the insect in its various growth stages. Depending on the species of insect, the growth phases can take a few days to a few weeks. In industrial insect farming, insects are bred primarily for food and for animal feed. From the production of insect eggs to the rearing of adult insects, industrial insect farming covers the various growth stages of insects. After the insects hatch from the eggs as larvae, they are usually stored in containers or boxes filled with substrate in prespecified environmental conditions, where they grow into adult insects. During storage in the containers, the larvae can also pupate into pupae, from which the adult insects grow. The substrate includes food for the larvae. The adult insects are "harvested", i.e. removed from the containers, and can then be further processed, e.g. into protein-rich end products such as oil or powder. Similarly to other industries, production facilities in industrial insect farming are also largely automated.

IN 2020/11046203 A discloses a system that automates the production of insect eggs. Two types of chambers are provided, with insects (black soldier flies) being bred in the first chamber. In a second chamber, egg-laying apparatuses are provided in which the bred black soldier flies lay their eggs. These egg-laying apparatuses are honeycomb-shaped and are located on the walls of the second chamber. The environmental conditions, such as temperature, light or humidity, in the chambers are regulated specifically for the keeping, reproduction and egg-laying of the insects.

WO 2022/081014 A1 also discloses a system for producing insect eggs, wherein a conveyor belt with a substrate is used as an egg-laying apparatus. Movable containers are arranged above the conveyor belt in which insects are kept as adult insects. There is a fine grid on the bottom of the containers. On the one hand, this prevents the adult insects kept in the containers from escaping from the containers. On the other hand, the substrate for egg laying is conveyed on the conveyor belt, and by lowering the containers onto the conveyor belt, the fine grid dips into the substrate, allowing the substrate to enter the containers. The adult insects then lay their eggs in the substrate on the conveyor belt. After the eggs have been laid, the containers are lifted off of the conveyor belt again and the eggs can be harvested from the conveyor belt.

During egg laying, it may happen that the adult insects do not lay their eggs in the egg-laying apparatuses provided for them, but in other openings, edges, corners, etc. that are present in the chambers or containers. This increases the effort required to harvest these eggs and the egg-laying apparatuses are therefore only partially filled with eggs.

SUMMARY

Embodiments optimize the production of insect eggs, in particular to improve egg laying and to simplify egg harvesting.

According to embodiments, an apparatus for producing insect eggs includes at least one attractant arranged in the region of the at least one egg-laying apparatus, which emits stimulants for the insects in order to lure the insects to the at least one egg-laying apparatus to lay the insect eggs when the container is used. At least one attractant is spatially separated from the at least one egg-laying apparatus and is separated from the container interior, and the stimulants emitted by the attractant pass through the at least one egg-laying apparatus into the container interior. As a result, when the apparatus is used, the insects in the container are induced to lay the insect eggs in the at least one egg-laying apparatus. As a result, the yield of insect eggs increases on the one hand and the effort required to harvest the insect eggs is reduced on the other.

Preferably, the at least one attractant is water and/or dead insects. This means that even the dead insects that, for example, accumulate at the bottom of the container can be reused.

In a preferred embodiment, the at least one egg-laying apparatus is perforated. Because the insects prefer to lay their eggs in particular in openings, perforation of at least one egg-laying apparatus is advantageous for egg laying.

Advantageously, the at least one egg-laying apparatus is arranged on a conveyor belt. This reduces the amount of work required, for example, to remove at least one egg-laying apparatus from the container in order to harvest the insect eggs.

Advantageously, the at least one egg-laying apparatus is at least partially removable from the conveyor belt. It is thus possible, for example to harvest the insect eggs, to remove only parts of the at least one egg-laying apparatus from the conveyor belt, thereby improving the handling of the at least one egg-laying apparatus.

In a preferred embodiment, the container has at least one outlet opening, wherein the at least one egg-laying apparatus on the conveyor belt extends at least partially through the at least one outlet opening. Due to the at least one outlet opening, it is not necessary to enter the container to harvest the insect eggs from the at least one egg-laying apparatus.

Preferably, water is arranged below the conveyor belt as the at least one attractant. Because insects prefer to lay their eggs near water, the position of the water below the conveyor belt is advantageous.

In an advantageous embodiment, the container comprises at least one insect conveying device that is designed to convey the insects into the container. This eliminates the need to manually introduce the insects into the container, which reduces the effort involved. In addition, the insect conveying device can allow the insects to be continuously and autonomously introduced into the container.

In a further advantageous embodiment, the container has a collecting device that is designed to collect the dead insects in the container and to arrange them in the region of the at least one egg-laying apparatus as the at least one attractant. On the one hand, this allows the interior of the container to be cleaned independently, which increases hygiene. On the other hand, the dead insects can be reused as at least one attractant.

In a preferred arrangement for producing insect eggs, a plurality of apparatuses are arranged in a row and/or stacked. To increase the production volume of insect eggs, the apparatuses can be arranged or expanded in a simple and space-saving manner, depending on the customer's requirements.

In a method according to the invention with the apparatus for producing insect eggs, at least one attractant is arranged in the region of the at least one egg-laying apparatus and the insects are lured by the attractant to the at least one egg-laying apparatus to lay the insect eggs. The insects in the container are thus guided to lay their eggs more specifically in the at least one egg-laying apparatus, thereby increasing the yield of insect eggs. This also simplifies the harvesting of insect eggs.

Advantageously, dead insects are collected in the container using a collecting device and the dead insects are provided as the at least one attractant of the at least one egg-laying apparatus. On the one hand, this removes the dead insects in order to keep the container interior clean and hygienic. On the other hand, the collected dead insects can easily be reused as at least one attractant.

Preferably, the insect eggs are removed from the at least one egg-laying apparatus at predetermined intervals, preferably once a day. In this way a continuous production of insect eggs can be achieved.

Advantageously, the insect eggs are removed from the at least one egg-laying apparatus mechanically or pneumatically or by flushing out with a liquid. This makes it easy to remove insect eggs, especially if they adhere to the egg-laying apparatus.

The insects are preferably conveyed into the container using at least one insect conveying device. This reduces the effort involved, as there is no need to manually introduce the insects into the container. In addition, the insects can be continuously and independently introduced into the container without the need to enter the container.

Embodiments are directed to an apparatus for producing insect eggs includes a container configured to accommodate insects in an interior of the container and to prevent the accommodated insects from escaping from the container; at least one egg-laying apparatus that is arranged in the container and is configured to accommodate insect eggs laid in the container by the accommodated insects; and at least one attractant arranged in an area of the at least one egg-laying apparatus that emits stimulants to lure the accommodated insects to the at least one egg-laying apparatus to lay the insect eggs. The at least one egg-laying apparatus is at least partially removable from the container, the at least one attractant is spatially separated from the at least one egg-laying apparatus and is separated from the container interior, and the stimulants emitted by the attractant pass through the at least one egg-laying apparatus into the container interior.

According to embodiments, the accommodated insects can be adult insects.

According to other embodiments, the at least one attractant may be at least one of water or dead insects.

In accordance with embodiments, the at least one egg-laying apparatus can be perforated.

In other embodiments, the at least one egg-laying apparatus may be arranged on a conveyor belt. The at least one egg-laying apparatus can be at least partially removable from the conveyor belt. Further, the container may have at least one outlet opening, and the at least one egg-laying apparatus on the conveyor belt can extend at least partially through the at least one outlet opening. Water can be arranged below the conveyor belt as the at least one attractant.

According to other embodiments, the container may include at least one insect conveying device configured to convey the insects into the container.

In other embodiments, the container may have a collecting device that is designed to collect dead accommodated insects in the container and to arrange the collected dead insects in the area of the at least one egg-laying apparatus as the at least one attractant.

Embodiments are directed to an arrangement that includes a plurality of the above-described apparatuses, in which the plurality of apparatuses are arranged in at least one of a row or stacked configuration.

Embodiments are directed to a method for producing insect eggs using the above-described apparatus that includes providing insects into an interior of the container; and positioning the at least one attractant in the area of the at least one egg-laying apparatus. The insects are lured to the at least one egg-laying apparatus by the attractant in order to lay the insect eggs.

In embodiments, the insects may be adult insects.

According to embodiments, dead insects can be collected in the container using a collecting device and the dead insects can be provided as the at least one attractant of the at least one egg-laying apparatus.

In accordance with embodiments, at predetermined intervals, the insect eggs may be removed from the at least one egg-laying apparatus. The predetermined intervals can be once per day.

In embodiments, the insect eggs can be removed from the at least one egg-laying apparatus mechanically or pneumatically or by flushing out with a liquid.

In accordance with still yet other embodiments, the providing of the insects can include conveying the insects into the interior of the container by at least one insect conveying device.

Other exemplary embodiments and advantages of the present invention may be ascertained by reviewing the present disclosure and the accompanying drawing.

Other exemplary embodiments and advantages of the present invention may be ascertained by reviewing the present disclosure and the accompanying drawing.

BRIEF DESCRIPTION OF THE DRAWINGS

The present invention is described in greater detail below with reference to FIGS. 1 to 4, which show exemplary, schematic, and non-limiting advantageous embodiments of the invention. In the figures.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
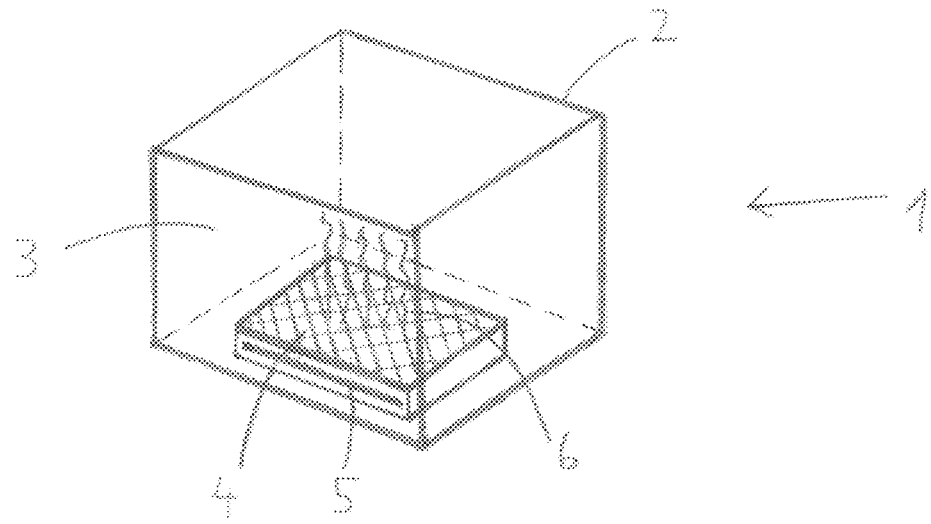
FIG. 1 shows the basic structure of the apparatus according to the invention.
Figure 3:
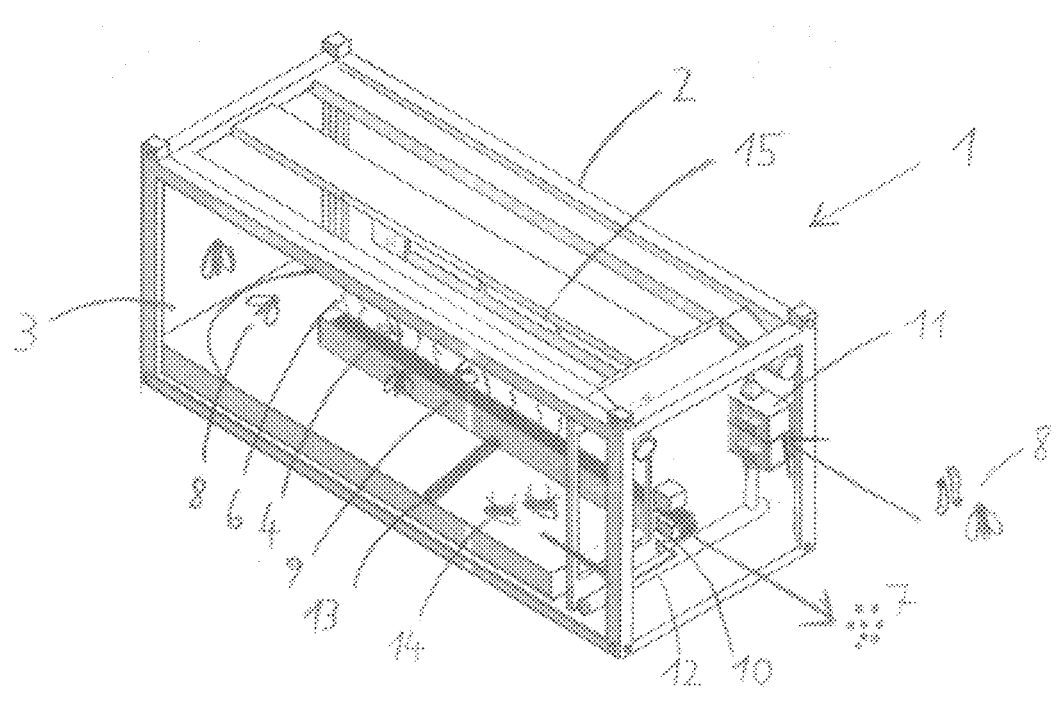
FIG. 3 shows an exemplary method for producing insect eggs.

FIG. 1 shows the basic structure of the apparatus 1 according to the invention for the production of insect eggs 7 (see FIG. 3). In this case, a container 2 is provided that is designed to accommodate insects 8 (see FIG. 3), in particular, adult insects, e.g., as flies, in a container interior 3 of the container 2 and to prevent the accommodated insects 8 from escaping from the container 2.

The container 2 can, for example, be rectangular, as shown in FIG. 1, although other shapes of the container 2 are of course also possible. The container interior 3 in FIG. 1 is in principle formed by four container walls, a container ceiling and a container bottom, wherein these can be designed differently. For example, they can be made of different materials, such as a plastic (e.g. acrylic glass), metal, wood, etc., wherein it is to be ensured that the insects 8 cannot escape from the container 2. The container 2 can also be constructed from a frame (e.g. made of metal), wherein the container walls and the container ceiling are made, for example, of a fine-mesh net (e.g., mosquito net).

Depending on the material for the container walls, the container ceiling and the container floor, ventilation and/or lighting of the container interior 3 (not shown) can be provided. When the apparatus 1 is used, conditions for the insects 8 can thus be created in the container interior 3 that ensure the survival of the insects 8, at least for a certain period of time, and promote egg laying (e.g., optimal air supply, temperature, humidity, light intensity, etc. in the container 2).

The container 2 can have a closable opening, such as a flap, door, removable wall, etc., in order to make the container interior 3 accessible via the opening as required, for example for cleaning, to put insects 8 into the container 2 or to remove the egg-laying apparatus 4.

In FIG. 1, an egg-laying apparatus 4 is shown in the container 2 by way of example, which is designed to accommodate insect eggs 7 laid in the container 2 by the insects 8 when the container 2 is used. Of course, a plurality of egg-laying apparatuses 4 can also be provided in the container 2. The egg-laying apparatus 4 can, as shown in FIG. 1, be designed as a mat, whereby the egg-laying apparatus 4 is preferably perforated, e.g., has circular cutouts (not shown). The egg-laying apparatus 4 can be made, for example, of a plastic, such as polyethylene, polypropylene or acrylonitrile-butadiene-styrene copolymers. Furthermore, the egg-laying apparatus 4 is preferably at least partially removable from the container 2. The egg-laying apparatus 4 could also be subdivided and consist of a plurality of egg-laying apparatus units (e.g., segments of the mat) that can be removed from the egg-laying apparatus 4 and from the container 2 in order to harvest the insect eggs.

The egg-laying apparatus 4 can also be colored to lure the insects to the egg-laying apparatus 4 when the container 2 is used. The egg-laying apparatus 4 can also be heated in order to lure the insects to the egg-laying apparatus 4 when the container 2 is used.

As shown in FIG. 1, at least one attractant 5 is arranged in the region of the egg-laying apparatus 4, which emits stimulants 6 for the insects 8 in order to lure the insects 8 to the egg-laying apparatus 4 to lay the insect eggs 7 when the container 2 is used. The attractant 5 is spatially separated from the at least one egg-laying apparatus 4 and is separated from the container interior 3, wherein the stimulants 6 emitted by the attractant 5 pass through the at least one egg-laying apparatus 4 into the container interior 3. In this context, "separated from the container interior 3" means that insects 8 are prevented from getting from the container interior 3 to the attractant 5. In this context, "spatially separated" means that the egg-laying apparatus 4 can be removed separately from the attractant 5. As indicated in FIG. 1 only by way of example, the attractant 5 is arranged in a box below the egg-laying apparatus 4, wherein the egg-laying apparatus 4 delimits the box at the top. The stimulants 6 emitted by the attractant 5 can pass through the egg-laying apparatus 4 into the container interior 3, for example through openings in the egg-laying apparatus 4. When the device 1 is used, the stimulants 6 lure the insects 8 in the container 2 to the egg-laying apparatus 4 to lay the insect eggs 7 there. In this case, the egg-laying apparatus 4 is designed accordingly to prevent the insects 8 from getting from the container interior 3 to the attractant 5 and laying their eggs there.

In this case, the attractant 5 is preferably water and/or dead insects 14 (see FIG. 3). The water as an attractant 5 can be present in liquid form or as an aerosol. Of course, the attractant 5 is not limited thereto and different attractants 5 can also be used. Furthermore, a fermented substance can be used as the attractant 5, as well as a mixture of different attractants 5. For example, the water can also be mixed with sugar or vinegar as an attractant 5. In addition, the at least one egg-laying apparatus 4 can also be perfumed with another attractant. The attractant 5 emits the stimulants 6, for example, in the form of a scent, which is perceived by the insects 8 and attracts the insects 8 to the egg-laying apparatus 4.

Figure 2:
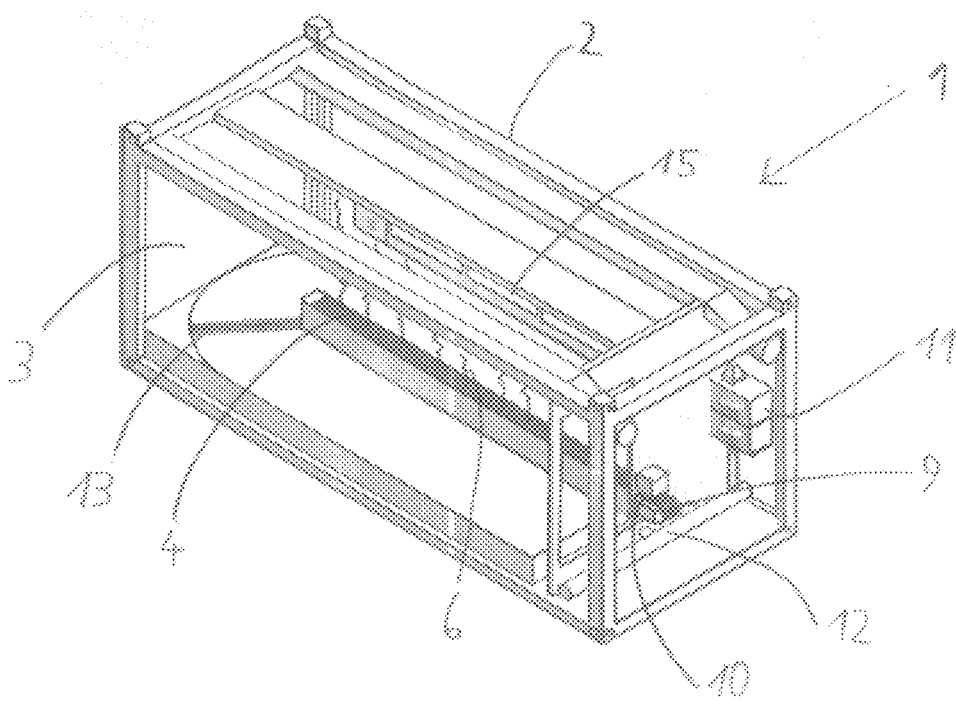
FIG. 2 shows a preferred embodiment of the apparatus according to the invention.

FIG. 2 shows a preferred embodiment of the apparatus 1 according to the invention for the production of insect eggs 7. In contrast to the basic structure of the device 1 in FIG. 1, the egg-laying apparatus 4 in FIG. 2 is arranged on a conveyor belt 9, wherein the egg-laying apparatus 4 is preferably at least partially removable from the conveyor belt 9 (e.g. as segments). In a further embodiment, a circulating belt of the conveyor belt 9 can also serve as the egg-laying apparatus 4. The container 2 has an outlet opening 10 in FIG. 1, wherein the egg-laying apparatus 4 on the conveyor belt 9 extends through the outlet opening 10. The attractant 5 is arranged below the conveyor belt 9 (not visible in FIG. 2), whereby it is spatially separated from the egg-laying apparatus 4. Furthermore, a housing of the conveyor belt 9 ensures that the attractant 5 is separated from the container interior 3. The stimulants 6 emitted by the attractant 5 can, as described in FIG. 1, enter the container interior 3 through the egg-laying apparatus 4.

As shown in FIG. 2, the container 2 preferably comprises an insect conveying device 11 that is designed to convey the insects 8 into the container 2. In this case, the insect conveying device 11 can be configured in different ways, e.g., as a conveyor belt or as a pneumatic conveyor that conveys the insects 8 into the container 2, e.g., with negative or positive pressure. Of course, the container 2 can also comprise a plurality of insect conveying devices 11. In FIG. 2, openings 15 are provided by way of example in the insect conveying device 11, through which openings the insects 8 can enter the container interior 3. The openings 15 can be permanently open, but can also be opened and closed, for example, mechanically, hydraulically or pneumatically. The insects 8 can also be conveyed, for example, as pupae with the insect conveying device 11, wherein adult insects 8 (e.g., flies) grow from the pupae, e.g., on a conveyor belt of the insect conveying device 11, which adult insects can enter the container interior 3 through the openings 15. The insects 8 could of course also grow in the container 2.

Preferably, the container 2 has a collecting device 12 that is designed to collect dead insects 14 (shown in FIG. 3) in the container 2 and to arrange them as the at least one attractant 5 in the region of the at least one egg-laying apparatus 4. For this purpose, a removal apparatus 13 (e.g., made of a plastic) can be provided in the container 2, which removal apparatus removes the dead insects 14 from the bottom of the container and transports them towards the collecting device 12. The collecting device 12 can, for example, comprise a pneumatic conveyor that is designed to arrange the collected dead insects 14 as the at least one attractant 5, for example below the conveyor belt 9. In addition, the collecting device 12 can also be designed to collect remains of the pupae that were conveyed with the insect conveying device 11 in order to also arrange them as the at least one attractant 5.

FIG. 3 shows an exemplary method for producing insect eggs 7 with the preferred embodiment of the apparatus 1 (see FIG. 2). The container 2 is filled with insects 8 (e.g., black soldier flies), which preferably enter the container interior 3 via the insect conveying device 11 and, for example, through the openings 15. The insects 8 in the container interior 3 are lured to the egg-laying apparatus 4 by the at least one attractant 5 below the conveyor belt 9, wherein the insects 8 lay the insect eggs 7 in the egg-laying apparatus 4.

Preferably, once a day the egg-laying apparatus 4 is conveyed out of the container 2 on the conveyor belt 9 through the outlet opening 10 (e.g. once along the entire length of the conveyor belt 9) in order to remove the insect eggs 7 from the egg-laying apparatus 4. In this case, the insect eggs 7 can be removed from the egg-laying apparatus 4 mechanically or pneumatically or by flushing out with a liquid (e.g. water). For this purpose, the container 2 can comprise an apparatus, such as an air blower, that removes the insect eggs 7 from the egg-laying apparatus 4 using compressed air. Another possibility would be that the egg-laying apparatus 4 is continuously conveyed on the conveyor belt 4 and the insect eggs 7 are thereby removed from the egg-laying apparatus 4.

As shown in FIG. 3, the dead insects 14 in the container 2 are collected by a collecting device 12, wherein a removal apparatus 13 pulls away the dead insects 14 on the container bottom and conveys them toward the collecting device 12. The collected dead insects 14 are then provided as the at least one attractant 5 of the egg-laying apparatus 4 in that the dead insects 14 are arranged below the conveyor belt 9.

Figure 4:
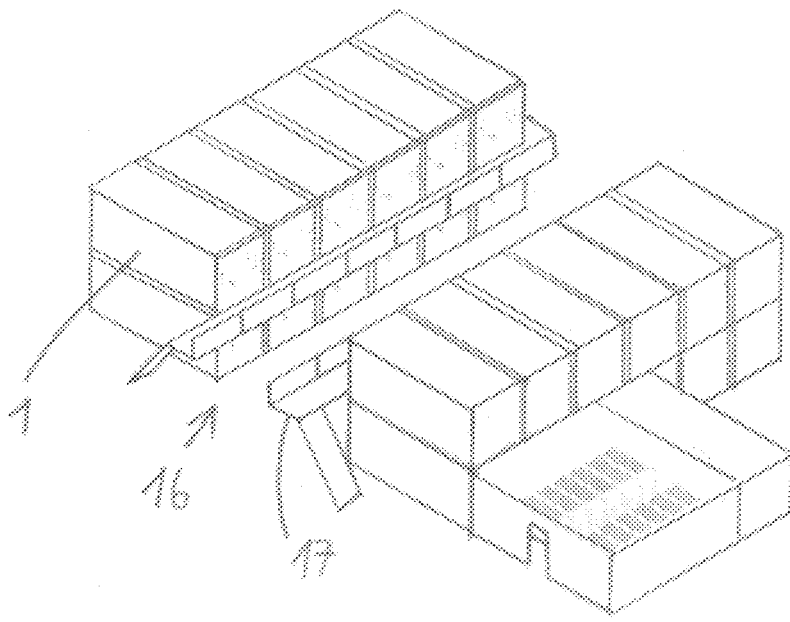
FIG. 4 shows a preferred arrangement of the apparatus according to the invention.

FIG. 4 shows a preferred arrangement 16 of the apparatus 1 according to the invention, wherein a plurality of apparatuses 1 are stacked and arranged in a row. For this purpose, the apparatus 1 can have connecting elements (not shown) that serve to connect apparatuses 1 to one another. In addition, platforms 17 can be provided to allow easy access to the apparatuses 1, e.g. for inspection and/or maintenance work. The apparatus 1 can, for example, further comprise lifting apparatuses (e.g., on the container 2, not shown) that serve to move the apparatus 1, e.g., by an industrial truck or a crane. Depending on customer requirements and/or production volumes, a plurality of apparatuses 1 for producing insect eggs 7 can be arranged differently.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. An apparatus for producing insect eggs, comprising:
   a container configured to accommodate insects in an interior of the container and to prevent the accommodated insects from escaping from the container;
   at least one egg-laying apparatus that is arranged in the container and is configured to accommodate insect eggs laid in the container by the accommodated insects; and
   at least one attractant arranged in an area of the at least one egg-laying apparatus that emits stimulants to lure the accommodated insects to the at least one egg-laying apparatus to lay the insect eggs,
   wherein the at least one egg-laying apparatus is removable from the container in order to harvest the insect eggs,
   wherein the at least one attractant is spatially separated from the at least one egg-laying apparatus and is separated from the container interior,
   wherein the stimulants emitted by the attractant pass through the at least one egg-laying apparatus into the container interior, and
   wherein the at least one egg-laying apparatus is arranged on a conveyor belt.

2. The apparatus according to claim 1, wherein the accommodated insects are adult insects.

3. The apparatus according to claim 1, wherein the at least one attractant is at least one of water or dead insects.

4. The apparatus according to claim 1, wherein the at least one egg-laying apparatus is perforated.

5. The apparatus according to claim 1, wherein the at least one egg-laying apparatus is removable from the conveyor belt.

6. The apparatus according to claim 1, wherein the container has at least one outlet opening, wherein the at least one egg-laying apparatus on the conveyor belt extends through the at least one outlet opening.

7. The apparatus according to claim 1, wherein water is arranged below the conveyor belt as the at least one attractant.

8. The apparatus according to claim 1, wherein the container comprises at least one insect conveying device that is configured to convey the insects into the container.

9. The apparatus according to claim 1, wherein the container has a collecting device that is designed to collect dead accommodated insects in the container and to arrange the collected dead insects in the area of the at least one egg-laying apparatus as the at least one attractant.

10. An arrangement of a plurality of the apparatuses according to claim 1, wherein the plurality of apparatuses are arranged in at least one of a row or stacked configuration.

11. A method for producing insect eggs using the apparatus according to claim 1, comprising:

providing insects into an interior of the container; and positioning the at least one attractant in the area of the at least one egg-laying apparatus, whereby the insects are lured to the at least one egg-laying apparatus by the attractant in order to lay the insect eggs.

12. The method according to claim 11, wherein the insects are adult insects.

13. The method according to claim 11, wherein dead insects are collected in the container using a collecting device and the dead insects are provided as the at least one attractant of the at least one egg-laying apparatus.

14. The method according to claim 11, wherein, at predetermined intervals, the insect eggs are removed from the at least one egg-laying apparatus.

15. The method according to claim 14, wherein the predetermined intervals are once per day.

16. The method according to claim 14, wherein the insect eggs are removed from the at least one egg-laying apparatus mechanically or pneumatically or by flushing out with a liquid.

17. The method according to claim 11, wherein the providing of the insects comprises conveying the insects into the interior of the container by at least one insect conveying device.

18. The apparatus according to claim 1, wherein the apparatus has connecting elements to connect apparatuses to one another.

19. The apparatus according to claim 1, wherein a circulating belt of the conveyor belt is designed to serve as the egg-laying apparatus.

20. The apparatus according to claim 1, wherein the conveyor belt comprises a housing, which ensures that the attractant is separated from the container interior and that the stimulants emitted by the attractant enters the container interior through the egg-laying apparatus.

* * * * *